(12) United States Patent
Nagel (10) Patent No.: US 7,651,874 B2
(45) Date of Patent: Jan. 26, 2010

(54) METHOD AND APPARATUS FOR LOCALIZING PRODUCTION ERRORS IN A SEMICONDUCTOR COMPONENT PART

(75) Inventor: Henning Nagel, Untergruppenbach (DE)

(73) Assignee: Schott Solar AG, Alzenau (DE)

( * ) Notice: Subject to any disclaimer, the term of this patent is extended or adjusted under 35 U.S.C. 154(b) by 401 days.

(21) Appl. No.: 11/465,859

(22) Filed: Aug. 21, 2006

(65) Prior Publication Data

US 2007/0048884 A1 Mar. 1, 2007

(30) Foreign Application Priority Data

Aug. 23, 2005 (DE) .................. 10 2005 040 010

(51) Int. Cl.
*H01L 21/66* (2006.01)
(52) U.S. Cl. .............................. 438/17; 438/16; 438/18; 438/69; 257/E21.521; 324/501
(58) Field of Classification Search .................. 438/7, 438/10, 11, 16–18, 57, 60, 69; 257/414, 257/428, 431, 432, E31.001, E25.001, E25.007, 257/E25.009, E21.521; 324/501
See application file for complete search history.

(56) References Cited

U.S. PATENT DOCUMENTS

| 4,661,770 | A | * | 4/1987 | von Roos | .................... | 324/767 |
| 4,967,152 | A | | 10/1990 | Patterson | | |
| 5,006,717 | A | | 4/1991 | Tsutsu et al. | | |
| 6,154,034 | A | * | 11/2000 | Lovelady et al. | ............ | 324/501 |
| 6,750,662 | B1 | | 6/2004 | Van Der Heide | | |
| 6,812,047 | B1 | * | 11/2004 | Borden et al. | ................. | 438/16 |
| 2005/0252545 | A1 | | 11/2005 | Nowlan et al. | | |

FOREIGN PATENT DOCUMENTS

EP 0216077 4/1987

OTHER PUBLICATIONS

Fuyuki, T., Kondo, H., Kaji, Y., Yamazaki, T., Takahashi, Y., and Uraoka, Y. "One Shot Mapping of Minority Carrier Diffusion Length in Polycrystalline Silicon Solar Cells Using Electroluminescence." Photovoltaic Specialists Conference, Jan. 3-7, 2005. Japan: Nara Institute of Science and Technology, 2005. 1343-1345.*
Ng, Kwok K. Complete Guide to Semiconductor Devices Second Edition. New York: John Wiley & Sons, Inc. 2002.*

(Continued)

*Primary Examiner*—Zandra Smith
*Assistant Examiner*—Christy L Novacek
(74) *Attorney, Agent, or Firm*—Dennison, Schultz & MacDonald (57) ABSTRACT

The invention relates to a method and to an arrangement for localizing production errors in a semiconductor component part by generating excess charge carriers in the semiconductor component part and by determining the electric potential in said part. In order to be able to localize production errors with simple measures and without damaging the semiconductor component part, it is suggested that the semiconductor component part be stimulated to become luminescent and that the locally resolved luminescence intensity distribution be determined in order to determine the locally resolved distribution of the electric potential in the semiconductor component part.

9 Claims, 5 Drawing Sheets

OTHER PUBLICATIONS

Ferraioli et al "Current-Voltage Characteristics of High-Efficiency Silicon Solar Cell from Photoluminescense", Applied Physics Letters, 2004, vol. 85, pp. 4222-4224.

Fuyuki et al "Photographic Surveying of Minority Carrier Diffusion Length in Polycrystalline Silicon Solar Cells by Electroluminescence" Applied Physics Letters, 2005, vol. 86, pp. 262108-1-262108-3.

Ostapenko et al, "Defect Monitoring Using Scanning Photoluminescence Spectroscopy in Multicrystalline Silicon Wafers", Semiconductor, Science and Technology, Aug. 2000, pp. 840-848.

Ostapenko et al, "Defect Mapping in Full-size Multi-crystalline Si Wafers", The EP Physical Journal, Jul. 2004, pp. 55-58.

Koshka et al, "Scanning Room-Temperature Photoluminescence In Polycrystalline Silicon", Applied Physics Letters, Mar. 1999, pp. 1555-1557.

* cited by examiner

X = Localization coordinate

Y = Electric potential, luminescence intensity

METHOD AND APPARATUS FOR LOCALIZING PRODUCTION ERRORS IN A SEMICONDUCTOR COMPONENT PART

BACKGROUND OF THE INVENTION

The invention relates to a method for localizing production errors in a semiconductor component part by generating excess charge carriers in the semiconductor component part and by determining the electric potential in said part. In addition, the invention makes reference to an arrangement for localizing production errors in a semiconductor component part, said arrangement comprising at least one first device for the generation of excess charge carriers in the semiconductor component part.

Document U.S. Pat. No. 6,750,662 discloses a method and an apparatus of the aforementioned type. In this case, the electric potential distribution in the semiconductor component part is measured with metal tips that produce an electric contact with the semiconductor surface at several positions. In order to generate excess charge carriers, either a voltage is applied to the semiconductor component part, i.e., it is connected to an external electric circuit, or the semiconductor component part is exposed to electromagnetic radiation.

In order to determine the locally resolved electric potential distribution, a wire is scratched across the surface of the semiconductor component part, thereby damaging said component part. This is disadvantageous, in particular if—as is usual—an insulating anti-reflection layer is applied to the surface, through which the needle needs to pass. The resultant mechanical damage makes them unsuitable for use in solar cells. Apart from that appropriate measurements require relatively much time.

In order to localize production errors in an electrical conductor, focused UV light is applied to the conductor in order to then measure the energy of the electrons ejected from the conductor (U.S. Pat. No. 4,967,152).

Document EP-A-0 216 077 uses photoelectron emission spectroscopy to test an integrated circuit in a non-contact manner.

SUMMARY OF THE INVENTION

The object of the present invention is to develop a method and an apparatus of the aforementioned type in such a manner that production errors can be localized with simple measures and without damaging the semiconductor component part. Also, it should be possible to carry out the measurements within a short time.

Referring to the method, the object of the invention essentially provides that the semiconductor component part be stimulated to become luminescent and that the luminescence intensity distribution be determined in order to determine the distribution of the electric potential in the semiconductor component part.

By itself, or when used in combination, the term luminescence is defined in terms of the general situation of photoluminescence or electroluminescence. Preferably, in accordance with the invention, however, the electroluminescence intensity distribution is utilized to determine the locally resolved electric potential distribution in the semiconductor component part.

In accordance with the invention, a non-contact measurement of the electric potential distribution in the semiconductor component part is performed, whereby the measurement itself can be performed extremely rapidly, if necessary, in fractions of seconds.

Experience has shown that a high charge carrier recombination rate results in a high intensity. However, a high charge carrier recombination means that a high excess charge carrier density, and thus a high electric potential, exist.

Indeed, it has been known to measure the luminescence intensity in semiconductor component parts in order to detect inhomogeneities with regard to the effective useful life of the charge carriers. In so doing, it is possible to stimulate luminescence either with high-energy photons (S. Ostapenko and M. Romero, Eur. Phys. J. Appl. Phys. 27, 2004, p. 55) or by the injection of excess charge carriers (T. Fuyuki, H. Kondo, T. Yamazaki, Y. Uraoka (Applied Physics Letters 86, 2005, 5261108-1-262108-3). In the first case, reference is made to photoluminescence, in the second case to electroluminescence. In accordance with T. Fuyuki et al, the locally resolved luminescence intensity determination occurs in order to be able to provide information regarding the diffusion length of minority charge carriers, i.e., their useful life, and thus regarding the quality of the semiconductor layers.

However, the luminescence intensity distributions are not used to draw conclusions regarding the electric potential, i.e., in a locally resolved manner, in order to localize in particular errors regarding the current-discharging conductor tracks in solar cells, i.e., to control conductor track interruptions or conductor track constrictions, and/or the conductivity of conductor tracks.

In addition, literature reference US.Z.: Applied Physics Letters, 2004, pp. 4222-4924, has disclosed that the mean value of the photoluminescence of a solar cell should be measured across all the solar cell surfaces in order thus compute the mean electrochemical potential at the pn transition. As a result, a solar cell displaying a current-voltage curve without ohmic losses in the contact conductor tracks and on the metal semiconductor contact is determined, without thereby allowing a control of the production errors themselves.

In order to generate the excess charge carriers required to generate luminescence, one suggestion of the invention provides that the semiconductor component part be connected in an external electric circuit in such a manner that the resultant electric potential differences lead to a spatially different charge carrier concentration and thus to a luminescence intensity exhibiting different spatial strength. Alternatively or additionally, electromagnetic radiation is used to stimulate luminescence locally or over a large area.

In particular, this provides that the measurement of luminescence intensity is carried out in the wavelength range suitable for the semiconductors that are used, preferably with an areal camera, a line camera or a screening detector. Among the selected conditions, the spatial luminescence intensity distribution represents a direct measure of the spatial electric potential distribution.

The inventive teaching results, in particular, in the following advantages:

Short measuring times of to below 0.5 sec.;

electrical contacting is required only at a few points or not at all. Therefore, any damage to the sensitive semiconductor surface is basically prevented; insulating layers on the semiconductor surface are neither damaged nor do they need to be removed if they are transparent to luminescent radiation;

by aligning or focusing the detector that captures the luminescent radiation and/or an optionally available illumination generating the excess charge carriers, great flexibility with respect to the measuring ranges and the local resolutions to be detected is given, so that, in particular, semiconductor component parts can be measured with the same apparatus, independent of the expanse of their area.

A development of the invention provides that the luminescence intensity and/or its spatial distribution be measured for a minimum of two different electric current densities prevailing in the semiconductor component part, and that the electric potential distribution in the semiconductor component part be determined based on the difference of the luminescence intensity distributions measured for the respective electric current densities.

In order to make possible a localization of existing errors based on the luminescence intensity measurement and the electric potential distribution directly resulting therefrom, it is intended that the luminescence intensity distribution of the semiconductor component part and its optical image be superimposed.

In accordance with the invention, the luminescence intensity distribution is measured in a locally resolved manner, and the locally resolved luminescence intensity distribution is used to determine the areal and/or spatial distribution of the electric potential in the semiconductor component part. In so doing, the semiconductor component part that is used is, in particular, a solar cell.

In particular, the invention is characterized by a method for localizing conductor track interruptions and/or conductor track constrictions in a solar cell and/or of checking the electrical conductivity of the conductor tracks in a solar cell, in which case the solar cell is stimulated to luminescence, preferably electroluminescence, and its locally resolved intensity distribution is determined for the determination of the locally resolved distribution of the electric potential in the solar cell. In accordance with the invention, the measured electroluminescence distribution is used to determine the electric potential distribution, in which case a qualitative or quantitative determination may take place. Basically, however, a qualitative determination is adequate for the detection of defective conductor tracks.

In accordance with the invention, based on the luminescence intensity, conclusions are drawn with respect to the electric potential distribution in the solar cell; this, in turn, allows conclusions regarding defective and/or improperly connected conductor tracks.

Figure 12:
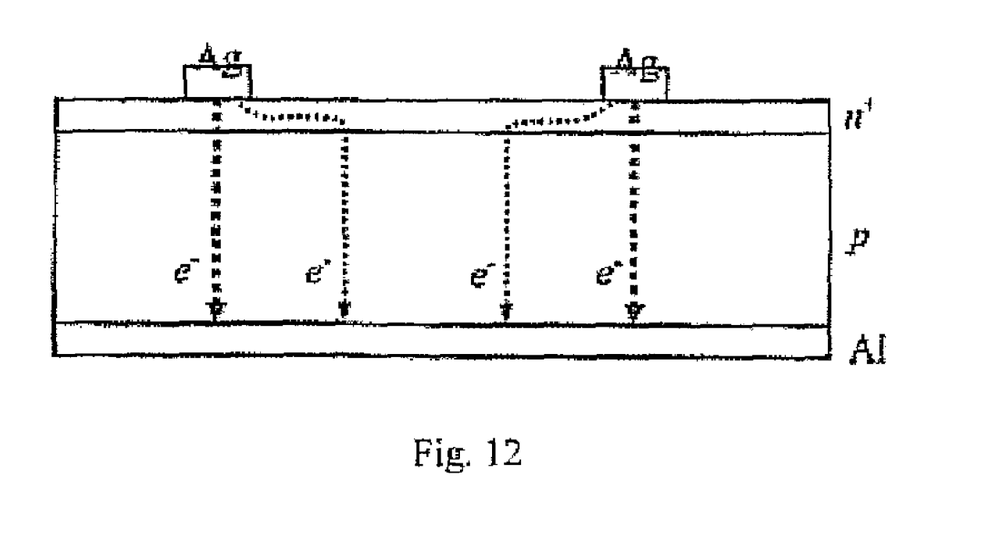

Referring to FIG. 12, only the principle of the physical processes that are the basis of the invention will be explained. This drawing shows, schematically, the flow of current in a solar cell, which, in the exemplary embodiment, comprises front contacts consisting of Ag and one rear contact consisting of Al.

Due to ohmic losses in the $n^+$-diffused layer, the electric potential is greatest at the Ag contacts on the front side of the solar cell and drops off toward the middle between two Ag contact fingers. Therefore, the current density across the pn transition is highest in the vicinity of the front-side contacts and lowest in the middle between the front-side contacts. Again, the concentration of excess charge carriers ($e^-$ in the p-doped area) is greatest wherever the current density is greatest. The radiating recombination rate and thus the luminescence intensity are proportional to the concentration of the excess charge carriers.

The inventive method is preferably intended for the examination of conductor track interruptions and/or conductor track constrictions of a solar cell, and/or for the examination of the electrical conductivity of the conductor tracks of a solar cell.

Another suggestion provides that the semiconductor component part be illuminated locally and that the spatial luminescence intensity distribution be measured in the vicinity of the illumination site. Further, the spatial luminescence intensity distribution in the vicinity of the illumination site can be used to determine the layer resistance of one or more conductive semiconductor layers.

An arrangement of the aforementioned type is characterized in that a detector detecting the luminescence of the semiconductor component part is associated with the semiconductor component part or with one or more of the areas of said semiconductor component part. In so doing, this may be, in particular, a CCD line camera or a CCD matrix camera which is arranged, optionally adjustably, relative to the semiconductor component part. This is particularly advantageous when large-area semiconductor component parts are to be inspected, so that only one arrangement is required.

Furthermore, the semiconductor component part that is to be examined is connected with an external electric circuit for generating excess charge carriers, and/or the semiconductor component part is exposed to illumination for generating the excess charge carriers.

BRIEF DESCRIPTION OF THE DRAWINGS

Additional details, advantages and features of the invention result from the claims, from the features—by themselves and/or in combination—of said claims, as well as from the preferred exemplary embodiments as illustrated by the following description of the drawings.

They show in

DESCRIPTION OF THE PREFERRED EMBODIMENTS

These Figures, which fundamentally depict the same elements with the same reference numbers, basically show arrangements for detecting and localizing production errors in semiconductor component parts, as well as images of luminescence distributions in said semiconductor component parts.

Figure 1:
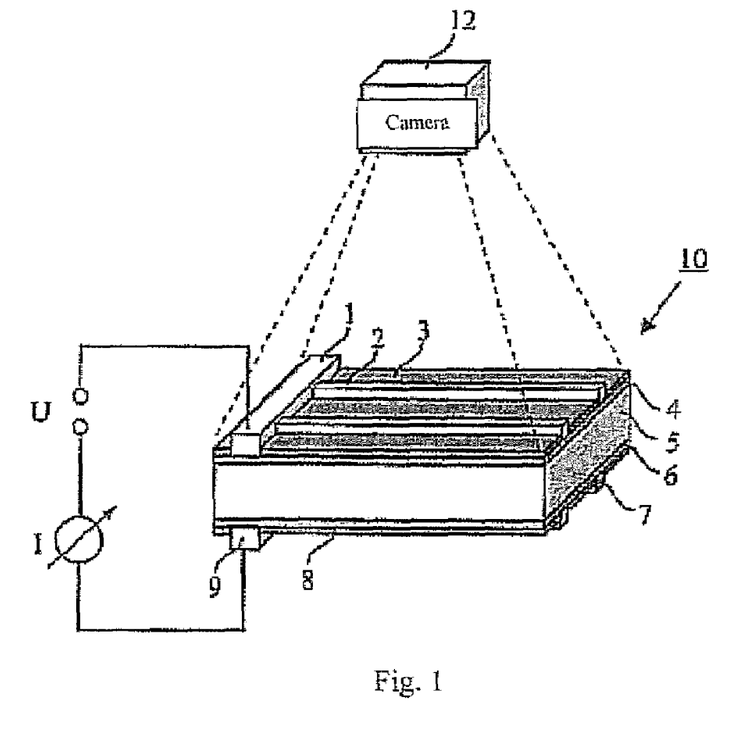
FIG. 1 a first embodiment of an arrangement for detecting and localizing production errors in a semiconductor component part.

FIG. 1 shows, in a strictly schematic manner, a first embodiment of such an arrangement. This arrangement is to be used to check a semiconductor component part having the configuration of a monocrystalline silicon solar cell 10 for production errors. Here, priority is given to production errors in power bus bars and current conductor tracks connected to these bus bars.

Referring to FIG. 1, the solar cell 10 comprises, on its front and rear sides, metal power bus bars 1, 9, as well as thinner metallic conductor tracks 2, 7 that are connected with the latter power bus bars and extend perpendicularly with respect to the power bus bars 1, 9.

The solar cell 10 consists, for example, of a silicon panel 5 which has a thickness of approximately 250 μm and is provided with p-doping that is $n^+$-diffused on the entire area of the front side 4 and $p^+$-diffused on the entire area of the rear side 6. Further, the front and rear sides 4, 6 are provided with anti-reflection layers 3, 8, said layers specifically consisting of SiN.

On the power bus bars 1, 9, the solar cell 10 is electrically connected in series to a voltage source U and an ammeter I. Above the solar cell 10, a detector 12 is arranged, which, in the exemplary embodiment, is configured as a camera with a cooled CCD chip. The sensitivity of the camera is designed for a wavelength range between 700 nm and 1200 nm.

In order to localize production errors in the semiconductor component part configured as a solar cell 10 in the exemplary embodiment, i.e., specifically in the region of the power bus bars 1, 9 and the current conductor tracks 2, 7, the procedure in accordance with the method herein can be the following.

In view of the direction of transmission, a voltage is applied to the solar cell 10 in such a manner that excess charge carriers occur in the solar cell 10, said excess charge carriers resulting in a luminescence having an intensity that can be measured locally resolved by the camera 12 in order to determine, based on this, the spatial distribution of the electric potential in the solar cell 10, which, in turn, allows conclusions to be drawn regarding production errors.

Figure 2:
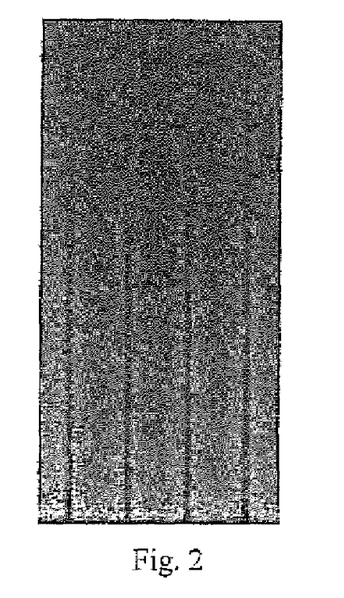
FIG. 2 a grayscale image of an area of the semiconductor component part in accordance with FIG. 1.

For example, a voltage of 0.62 V can be applied to a monocrystalline solar cell having a fully metallized rear side and no anti-reflection layer on the rear side. The current density through the solar cell 10 is 35 mA/cm³ in the direction of transmission. Using the apparatus shown in FIG. 1, the luminescence intensity of a region of the solar cell 10 is locally resolved within 0.8 sec. FIG. 2 shows the result as a grayscale image. Light-color areas correspond to high luminescence intensity, dark-color areas to those displaying lower intensity. The dark lines extending in perpendicular direction should not be associated with the luminescent thin metallic conductor tracks on the front side of the solar cell, i.e., referring to the exemplary embodiment, the conductor tracks 2. On the lower edge of the illustration, a part of the likewise not luminescent metallic power bus bar 1 is shown. In the immediate vicinity of these metallic areas, an increased luminescence intensity of the solar cell due to the increased electric potential can be recognized. Referring to FIG. 2, lighter-color areas correspond to a higher electric potential, darker-color areas correspond to a lower electric potential. Referring to FIG. 2, the grayscales represent a direct measure of the electric potential in the region outside the metallic areas. The reason for the increased electric potential in the immediate vicinity of the metallic areas is ohmic losses in the $n^+$-diffused front layer 4. In addition, FIG. 2 shows an increase of the electric potential from the top to the bottom, which could be attributable to the fact that only the lower power bus bar 1 is in electrical contact with the external electric circuit. The measured electric potential distribution makes clear that there are no production errors in the inspected region of the solar cell.

The previously given exemplary numerical values must be varied, of course, as a function of the semiconductor component part that is to be examined and thus must not be considered as narrowing the invention.

Figure 3:
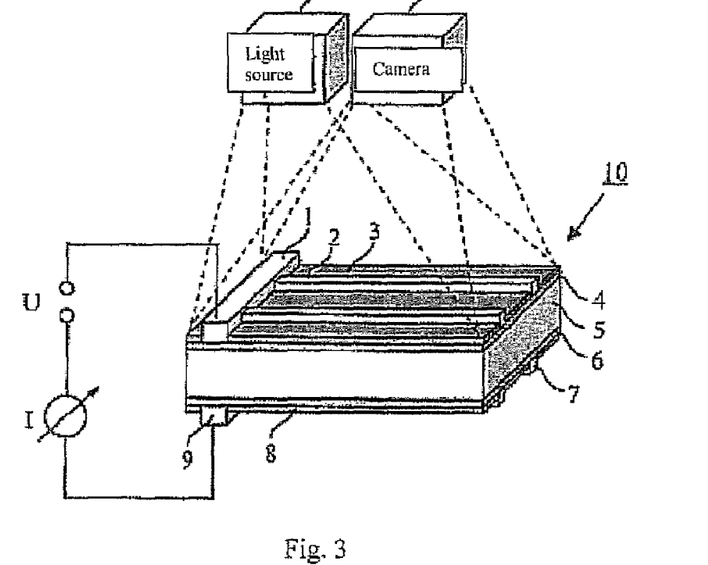
FIG. 3 a second embodiment of an arrangement for detecting and localizing production errors in a semiconductor component part.

FIG. 3 shows another exemplary embodiment of an arrangement for detecting and localizing production errors in semiconductor component parts, in which case elements corresponding to those in FIG. 1 have the same reference numbers.

Supplementary to the aforementioned methods, the solar cell 10 is illuminated with a light source 14 while the luminescence intensity is being measured. Consequently, charge carriers are generated in the semiconductor, so that the same electric potential distribution occurs as in the case of a specific use of the solar cell 10. In addition, reflecting regions such as, e.g., the metallic conductor tracks 1, 2, can be rendered identifiable if the camera 12 is sensitive in the wavelength range of the reflected light. In this case, a superimposition of the optical image and the spatial luminescence intensity distribution is attained. This allows the simple differentiation between the semiconductor region displaying low luminescence intensity and regions, in which there are no areas that are transparent to luminescence radiation, such as, e.g., the metallic conductor tracks 1, 2.

Referring to the arrangement in accordance with FIG. 3, it is not absolutely necessary that the solar cell 10 be connected to the external electric circuit that contains the voltage source U. This corresponds to an embodiment of FIG. 6, in which the external electric circuit comprises an adjustable resistor R. The current itself is generated by the solar cell 10. Basically, however, a voltage application should occur in order to generate a sufficient quantity of excess charge carriers and thus the luminescence required for taking measurements.

Referring to FIG. 3, the shown basic arrangement was used to check a multicrystalline silicon solar cell for production errors. To accomplish this, a voltage of 0.62 V was applied, in which case the rear side of the silicon solar cell was frilly metallized and did not have an anti-reflection layer. The current density though the solar cell was 30 mA/cm³ in the direction of transmission.

Figure 4:
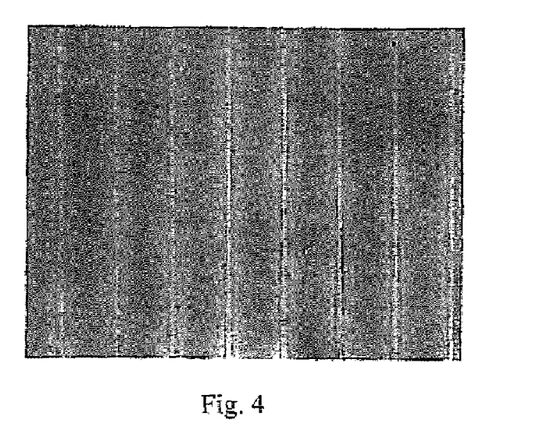
FIG. 4 an image of a section of the semiconductor component part in accordance with FIG. 3.

FIG. 4 shows the image that was recorded with a CCD camera with a sensitivity in a wavelength range between 300 nm and 1200 nm. In this example, the auxiliary illumination displays an intensity that is so weak that the photogeneration rate of the charge carriers in the semiconductor can be ignored. Consequently, an electric potential distribution comparable to that of FIG. 2 occurs, this pointing to an error-free production process. In addition, the metallic conductor tracks 2 on the front side of the solar cell are light because they reflect the visible light more strongly than the anti-reflection-coated silicon of the front side 4 between the conductor tracks 2. This provides the advantage that the areas, in which the charge carriers have a reduced effective useful life and in which the excess charge carrier density is reduced and thus a lower luminescence intensity is displayed, can easily be distinguished from the areas which are covered by the conductor tracks 2. Areas displaying reduced effective useful life of the charge carriers are found regularly in multicrystalline silicon. FIG. 4 shows such a region on the upper right-hand side.

Figure 5:
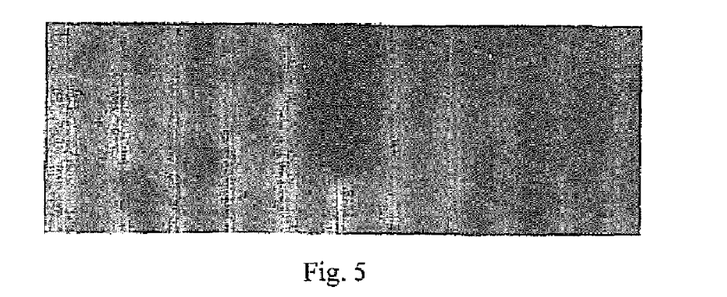
FIG. 5 an image of a section of a multicrystalline silicon solar cell, measured with an arrangement in accordance with FIG. 3.

FIG. 5 shows an image of a multicrystalline silicon solar cell which was measured under the same conditions as described above. The electric contact occurs on a not visible power bus bar at the lower edge of the image. The dark area in the middle of FIG. 5 corresponds to a region displaying low electric potential due to an interruption of one of the middle conductor tracks 2, said interruption being barely visible with the naked eye. The conductor track 2 itself can be seen well as a light-color line in the dark area due to the auxiliary illumination.

Figure 7:
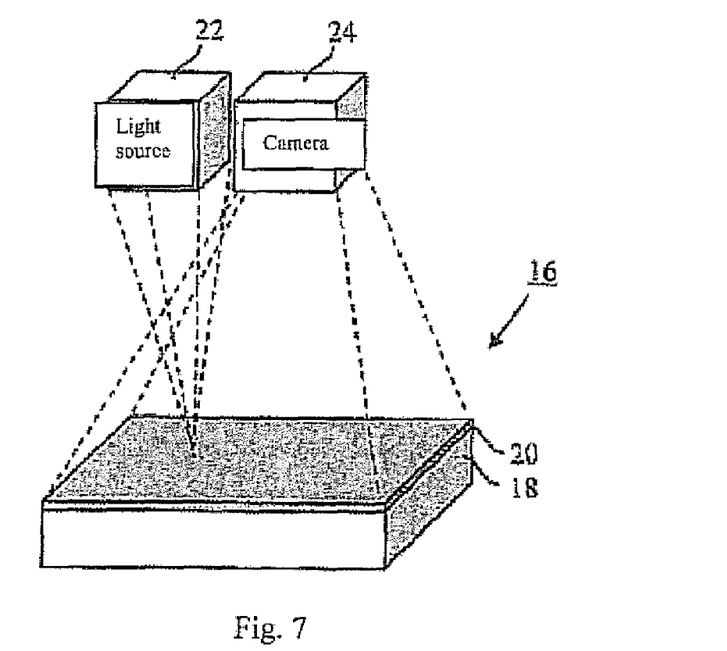
FIG. 7 a fourth embodiment of an arrangement for detecting and localizing production errors in a semiconductor component part.

FIG. 7 shows another basic illustration of an exemplary embodiment of an inventive arrangement for detecting and localizing production errors in semiconductor component parts. In this exemplary embodiment, the semiconductor component part 16 is a crystalline silicon panel 18, which is p-doped and $n^+$-diffused over the entire area of the front side 20. A focused light source 22, ideally a laser, generates local excess charge carriers, so that an increased electric potential prevails in the illuminated region due to the charge-carrier-separating properties of the pn transition. Due to ohmic losses in the $n^+$-diffused layer 20, the potential drops outside the illuminated region. Based on the spatial luminescence distribution measured with a camera 24, such as a CCD matrix camera or a CCD line camera, the electric potential distribution around the illuminated region is determined. This results in the layer resistance of the $n^+$-diffused layer 20. By scanning the entire silicon panel 16, the layer resistance can be measured locally resolved. In so doing, the example illustrates that, with the use of the inventive teaching, a non-contact quality control of thermic processes for the diffusion of doping substances becomes possible in a simple and ideal manner.

Figure 6:
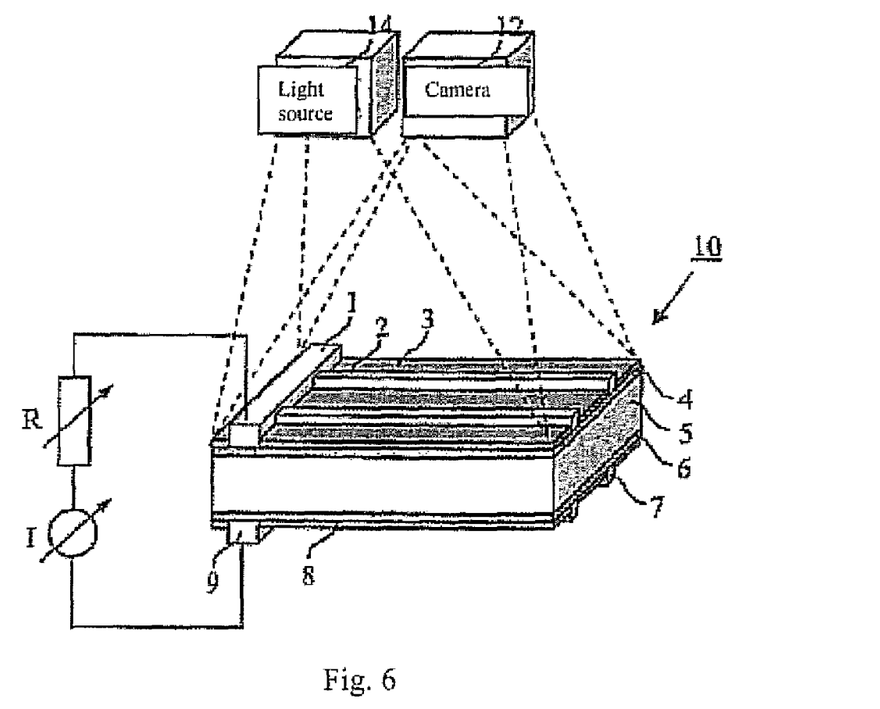
FIG. 6 another embodiment of an arrangement for detecting and localizing production errors in a semiconductor component part.

If, referring to FIGS. 3, 6 and 7, light sources such as light sources 14, 22 are used to generate excess charge carriers in semiconductors, typically a high intensity of $>500$ W/m$^2$ is used for these light sources. The wavelength range should be outside (mostly below) the wavelength range of the luminescence, so that there is no interference with the luminescence detector. An optical bandpass filter, which displays high transmissiveness in the wavelength range of the luminescence and very low transmissiveness outside this range, is potentially provided upstream of the detector. Silicon solar cells luminesce at high intensity in the wavelength range between 1000 and 1300 nm. The luminescence of silicon can be measured between 440 and 1800 nm. Typically, light having wavelengths between 300 and 850 nm is used for the generation of excess charge carriers, in particular since the coefficient of absorption of silicon is very high in this range. For the local generation of excess charge carriers (light source 22), a helium-neon laser having a wavelength of 632.8 nm is well-suited.

To the extent that—in accordance with FIGS. 3 and 6—the light source is used only for the superimposition of an optical image, a very low intensity is used, e.g., 0.5 W/m$^2$. As concerns the wavelength range, the only applicable condition is that the camera must be sensitive enough. Therefore, e.g., light from a neon fluorescent tube or from a halogen lamp having wavelengths greater than 200 nm is used with cameras used for silicon solar cells.

Figure 11:
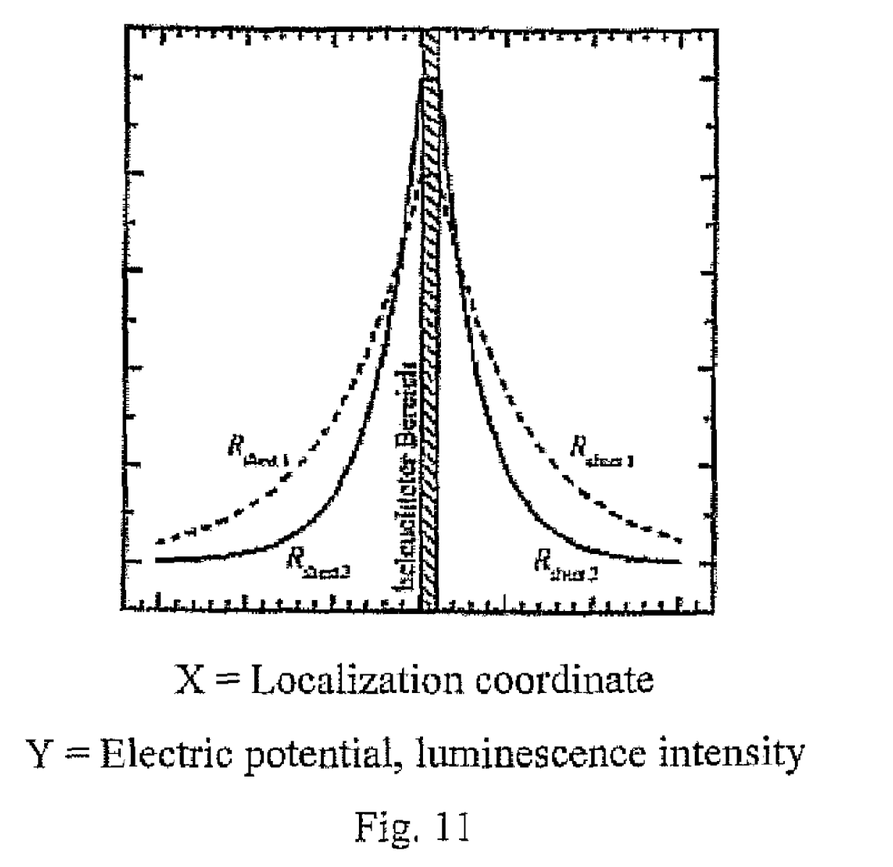
FIG. 11 a location-dependent curve of the electric potential and the luminescence intensity in a semiconductor component part; and, FIG. 12 a basic diagram of a current flow in a solar cell.

Considering the inventive teaching, it is also possible to determine the layer resistance of one or more conductive semiconductor layers based on the spatial luminescence intensity distribution. Referring to a component part in accordance with FIG. 7, for example, the electric potential and the luminescence intensity with local illumination produce a curve as shown by FIG. 11. In so doing, $R_{sheet\ 1}$ and $R_{sheet\ 2}$ represent different levels of layer resistance of the $n^+$-diffused layer, whereby $R_{sheet\ 1} < R_{sheet\ 2}$ was assumed. The steeper the drop of the electric potential is outside the illuminated region, the greater is the layer resistance. The electric potential is determined based on the luminescence.

Figure 8:
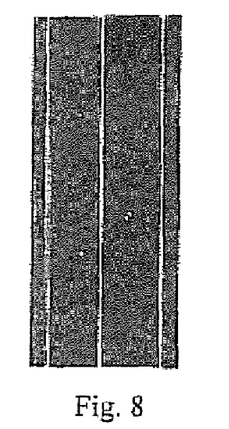
FIGS. 8-10 images of areas of a semiconductor component part displaying different luminescence intensities.
Figure 9:
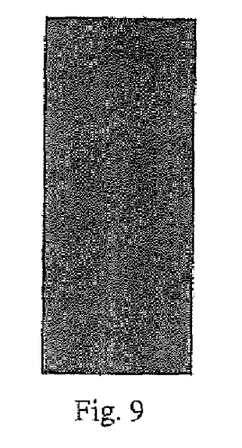
Figure 10:
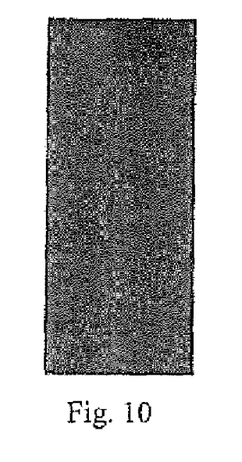

Referring to FIGS. 8 through 10, these are to explain additional measuring options for detecting and localizing production errors in semiconductor component parts. FIG. 8, for example, shows the luminescence intensity of a region of a multicrystalline silicon solar cell at a low current density of 10 mA/cm$^2$, whereby the luminescence intensity itself was measured in an arrangement in accordance with FIG. 1. Using the same arrangement, the luminescence of the same multicrystalline silicon solar cell was then measured at a high current density of 50 mA/cm$^2$ (FIG. 9). The voltage application to the multicrystalline silicon solar cell, in so doing, is effected in the direction of transmission. The solar cell used for measurement had a fully metallized rear side which consisted of aluminum and, locally, of silver, for soldering connectors thereto. At a low current density, the electric potential change in the region between the perpendicularly extending conductor tracks is negligible (FIG. 8), whereas this electric potential change is more pronounced at high current densities (FIG. 9). The latter is intensified by the exponential relationship between the electric potential and the luminescence intensity due to the pn transition. Referring to the upper right-hand side of FIG. 9, it can be seen in the area of the silver solder islands that the measured electric potential distribution is superimposed by the influence of the effective useful life of the charge carriers that is reduced in this area. This means that areas having charge carriers with reduced effective useful life can be confused with areas in which the electric potential is low. In order to eliminate this confusion, the spatial electric potential distribution can be determined, in accordance with the invention, in the solar cell and independent of the effective useful life of the charge carriers, in that the grayscale values of the images recorded at a high current density and at a low current density are subtracted from each other point by point. The result is shown by FIG. 10. This Figure shows the spatial electric potential distribution that has been corrected in view of the influence of the effective useful life of the charge carriers. It is obvious that regions displaying a different luminescence in the areas of the silver solder islands in FIGS. 8 and 9 do not indicate production errors.

The invention claimed is:

1. Method for localizing production errors in a solar cell semiconductor element having conductor tracks, comprising the steps of:
   generating excess charge carriers in the semiconductor element by stimulating the semiconductor element to become luminescent,
   determining electric potential in the stimulated element, by locally resolving luminescence intensity distribution, to determine thereby distribution of the electric potential in the semiconductor element, and
   determining electrical conductivity of the conductor tracks from the electrical potential.

2. Method in accordance with claim 1, wherein the luminescence intensity is determined by means of a COD matrix camera or a CCD line camera.

3. Method in accordance with claim 1, wherein the excess charge carriers are generated by applying an electric voltage to the semiconductor element.

4. Method in accordance with claim 1, wherein the excess charge carriers are generated by exposing the semiconductor element to electromagnetic radiation.

5. Method in accordance with claim 1, wherein the luminescence intensity is measured for a minimum of two different electric current densities prevailing in the semiconductor element, and electric potential distribution in the semiconductor element is determined based on a difference in the luminescence intensity distributions measured for the respective electric current densities.

6. Method in accordance with claim 1, wherein the luminescence intensity distribution of the semiconductor element is superimposed with an optical image thereof, in order to determine the electric potential distribution on and/or in the semiconductor component part.

7. Method in accordance with claim 1, wherein the locally resolved luminescence intensity distribution is used to determine an areal or spatial distribution of the electric potential in the semiconductor element.

8. Method in accordance with claim 1, for localizing conductor track interruptions and/or conductor track constrictions in the solar cell.

9. Method for localizing production errors in a semiconductor component part, comprising the steps of:

generating excess charge carriers in the semiconductor element by locally stimulating the element to become luminescent, determining electrical potential in the stimulated element by measuring spatial luminescence intensity distribution and using the distribution to determine the electric potential, and based on the determined electrical potential, determining layer resistance of at least one conductive layer in the semiconductor element.

\* \* \* \* \*